(12) United States Patent
Martens, III

(10) Patent No.: US 7,188,780 B2
(45) Date of Patent: Mar. 13, 2007

(54) VOLATILE MATERIAL EXPIRATION INDICATING SYSTEM

(75) Inventor: Edward J. Martens, III, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 247 days.

(21) Appl. No.: 10/880,634

(22) Filed: Jun. 30, 2004

(65) Prior Publication Data

US 2006/0000922 A1    Jan. 5, 2006

(51) Int. Cl.
*A61L 9/04*    (2006.01)
*B65D 73/00*    (2006.01)

(52) U.S. Cl. .................. 239/35; 239/34; 206/484.1; 428/905

(58) Field of Classification Search ................ 239/35, 239/34, 43, 55, 71, 74; 206/484.1, 484, 0.5, 206/524.8; 428/905, 29, 34.1; 422/120; 261/DIG. 65
See application file for complete search history.

(56) References Cited

U.S. PATENT DOCUMENTS

| | | | |
|---|---|---|---|
| 882,710 A | 3/1908 | Pearsall |
| 886,840 A | 5/1908 | Mueller |
| 1,204,934 A | 11/1916 | Burford et al. |
| 1,261,133 A | 4/1918 | Kidd |
| 1,802,999 A | 4/1931 | Budd |
| 2,268,529 A | 12/1941 | Stiles |
| 2,469,656 A | 5/1949 | Lienert |
| 2,550,954 A | 5/1951 | Benedict |
| 2,577,320 A | 12/1951 | Fenyo |
| 2,579,715 A | 12/1951 | Wilson et al. |
| 2,779,624 A | 1/1957 | Friedman |
| 3,178,844 A | 4/1965 | Christian |
| 3,424,380 A | 1/1969 | Curran |
| 3,558,055 A | 1/1971 | Storchheim |
| 3,790,081 A | 2/1974 | Thornton et al. |
| 3,804,330 A | 4/1974 | Miller, Jr. et al. |
| 3,948,445 A | 4/1976 | Andeweg |
| D243,402 S | 2/1977 | Irving |
| 4,009,384 A | 2/1977 | Holland |
| D247,573 S | 3/1978 | Schimanski |
| 4,157,787 A | 6/1979 | Schwartz |
| 4,158,440 A | 6/1979 | Sullivan et al. |
| 4,161,283 A * | 7/1979 | Hyman ...................... 239/55 |

(Continued)

FOREIGN PATENT DOCUMENTS

DE    84 90 017    3/1985

(Continued)

OTHER PUBLICATIONS http://www.glade.com/piso.asp.

(Continued)

*Primary Examiner*—Kevin Shaver
*Assistant Examiner*—Darren Gorman

(57) ABSTRACT

An indicator system with a dispenser providing controlled release of a volatile material contained within a dispenser, which indicates the exhaustion of the volatile material. The dispenser includes a blister that contains a vapor permeable membrane that collapses on a bottom wall due to internal vacuum forces created by the evacuation of volatile material. As the membrane collapses the remaining volatile material migrates to the periphery of the dispenser thereby indicating exhaustion of the volatile material.

28 Claims, 5 Drawing Sheets

U.S. PATENT DOCUMENTS

| | | | |
|---|---|---|---|
| 4,165,573 A | 8/1979 | Richards | |
| 4,170,080 A | 10/1979 | Bergh et al. | |
| 4,173,604 A | 11/1979 | Dimacopoulos | |
| 4,184,099 A | 1/1980 | Lindauer et al. | |
| 4,285,468 A * | 8/1981 | Hyman | 239/55 |
| 4,293,095 A | 10/1981 | Hamilton et al. | |
| D263,334 S | 3/1982 | Schimanski | |
| 4,327,056 A | 4/1982 | Gaiser | |
| D271,359 S | 11/1983 | Le | |
| D275,223 S | 8/1984 | Marxen | |
| D275,700 S | 9/1984 | Marxen | |
| 4,476,171 A | 10/1984 | Takeuchi | |
| 4,493,011 A | 1/1985 | Spector | |
| D279,146 S | 6/1985 | McCaffrey | |
| D280,363 S | 9/1985 | Wisecup, Jr. | |
| 4,549,250 A | 10/1985 | Spector | |
| 4,580,581 A | 4/1986 | Reece et al. | |
| 4,605,165 A | 8/1986 | Van Loveren et al. | |
| 4,614,299 A | 9/1986 | Van Loveren et al. | |
| D288,003 S | 1/1987 | Hoyt | |
| 4,634,614 A * | 1/1987 | Holzner | 428/34.2 |
| 4,695,435 A | 9/1987 | Spector | |
| 4,714,984 A | 12/1987 | Spector | |
| 4,720,409 A | 1/1988 | Spector | |
| D296,957 S | 8/1988 | Gordon et al. | |
| 4,762,275 A | 8/1988 | Herbert et al. | |
| 4,794,714 A | 1/1989 | Weisgerber | |
| 4,809,912 A | 3/1989 | Santini | |
| 4,814,212 A | 3/1989 | Spector | |
| 4,849,606 A | 7/1989 | Martens, III et al. | |
| 4,874,129 A | 10/1989 | DiSapio et al. | |
| 4,883,692 A | 11/1989 | Spector | |
| 4,898,328 A | 2/1990 | Fox | |
| 4,913,349 A | 4/1990 | Locko | |
| 4,917,301 A | 4/1990 | Munteanu | |
| 4,921,636 A | 5/1990 | Traas | |
| 4,939,858 A | 7/1990 | Dailey | |
| 4,979,673 A | 12/1990 | Wilk et al. | |
| 4,993,177 A | 2/1991 | Hudson | |
| 4,995,555 A | 2/1991 | Woodruff | |
| D320,266 S | 9/1991 | Kunze | |
| 5,060,858 A | 10/1991 | Santini | |
| D325,077 S | 3/1992 | Kearnes | |
| 5,148,983 A | 9/1992 | Muniz | |
| 5,148,984 A | 9/1992 | Bryson et al. | |
| 5,170,886 A * | 12/1992 | Holzner | 206/0.5 |
| 5,219,121 A | 6/1993 | Fox et al. | |
| 5,230,867 A | 7/1993 | Kunze et al. | |
| D339,238 S | 9/1993 | Hamilton | |
| 5,247,745 A | 9/1993 | Valentino | |
| 5,259,555 A | 11/1993 | Kiefer | |
| 5,297,732 A | 3/1994 | Hahn | |
| D346,068 S | 4/1994 | White | |
| 5,304,358 A | 4/1994 | Hoyt et al. | |
| 5,361,522 A | 11/1994 | Green | |
| 5,367,802 A | 11/1994 | Rosenberg | |
| 5,395,047 A | 3/1995 | Pendergrass, Jr. | |
| 5,402,517 A | 3/1995 | Gillett et al. | |
| D360,461 S | 7/1995 | Gillespie | |
| 5,439,100 A | 8/1995 | Gordon et al. | |
| D361,896 S | 9/1995 | Bramley et al. | |
| D366,107 S | 1/1996 | Shaffer | |
| 5,503,332 A | 4/1996 | Glenn | |
| D369,473 S | 5/1996 | Gluck | |
| 5,529,243 A | 6/1996 | Hoyt et al. | |
| 5,556,192 A | 9/1996 | Wang | |
| D376,002 S | 11/1996 | Upson | |
| D376,420 S | 12/1996 | Rymer | |
| 5,380,822 A | 7/1997 | Decker et al. | |
| 5,647,052 A | 7/1997 | Patel et al. | |
| 5,651,942 A | 7/1997 | Christensen | |
| D383,613 S | 9/1997 | Handler | |
| 5,679,334 A | 10/1997 | Semoff et al. | |
| 5,711,955 A * | 1/1998 | Karg | 424/409 |
| 5,716,000 A | 2/1998 | Fox | |
| D392,032 S | 3/1998 | Zaragoza et al. | |
| 5,735,460 A | 4/1998 | Eisenbraun | |
| 5,744,106 A | 4/1998 | Eagle | |
| 5,749,519 A | 5/1998 | Miller | |
| 5,749,520 A | 5/1998 | Martin et al. | |
| 5,782,409 A | 7/1998 | Paul | |
| 5,788,155 A | 8/1998 | Martin et al. | |
| 5,804,264 A | 9/1998 | Bowen | |
| D399,298 S | 10/1998 | Whitehead | |
| 5,845,847 A | 12/1998 | Martin et al. | |
| 5,875,968 A | 3/1999 | Miller et al. | |
| 5,885,701 A | 3/1999 | Berman et al. | |
| D407,809 S | 4/1999 | Hammond | |
| 5,899,382 A | 5/1999 | Hayes et al. | |
| 5,950,922 A | 9/1999 | Flinn | |
| 5,961,043 A | 10/1999 | Samuelson | |
| 5,975,427 A | 11/1999 | Harries | |
| 6,031,967 A | 2/2000 | Flashinski et al. | |
| 6,065,687 A | 5/2000 | Suzuki et al. | |
| 6,106,786 A | 8/2000 | Akahoshi | |
| 6,109,537 A | 8/2000 | Heath | |
| D431,075 S | 9/2000 | Barraclough | |
| 6,152,379 A | 11/2000 | Sorgenfrey | |
| 6,154,607 A | 11/2000 | Flashinski et al. | |
| D435,100 S | 12/2000 | Pesu et al. | |
| D437,404 S | 2/2001 | Wu | |
| D439,964 S | 4/2001 | Wu | |
| D441,441 S | 5/2001 | Upson | |
| D445,262 S | 7/2001 | Rowan | |
| 6,254,248 B1 | 7/2001 | McAuley et al. | |
| 6,254,836 B1 | 7/2001 | Fry | |
| D451,990 S | 12/2001 | Millet | |
| 6,328,935 B1 | 12/2001 | Buccellato | |
| D453,561 S | 2/2002 | Nelson | |
| 6,354,710 B1 | 3/2002 | Nacouzi | |
| 6,358,577 B1 | 3/2002 | Bowen et al. | |
| 6,363,734 B1 | 4/2002 | Aoyagi | |
| 6,367,706 B1 | 4/2002 | Putz | |
| D456,888 S | 5/2002 | Buthier | |
| D461,006 S | 7/2002 | Buthier | |
| 6,435,423 B2 | 8/2002 | Hurry et al. | |
| 6,478,440 B1 | 11/2002 | Jaworski et al. | |
| 6,548,015 B1 | 4/2003 | Stubbs et al. | |
| 6,555,068 B2 | 4/2003 | Smith | |
| D476,726 S | 7/2003 | Rosenberg | |
| 6,610,254 B1 | 8/2003 | Furner et al. | |
| D479,742 S | 9/2003 | Hollingsworth | |
| 6,618,974 B2 | 9/2003 | Szalay | |
| 6,627,857 B1 | 9/2003 | Tanner et al. | |
| D481,113 S | 10/2003 | Groene et al. | |
| 6,631,852 B1 | 10/2003 | O'Leary | |
| 6,638,591 B2 | 10/2003 | Bowen et al. | |
| D481,785 S | 11/2003 | Koike | |
| 6,643,967 B1 | 11/2003 | Bloom | |
| 6,648,239 B1 | 11/2003 | Myny et al. | |
| 6,663,838 B1 | 12/2003 | Soller et al. | |
| D485,607 S | 1/2004 | Wu | |
| D487,308 S | 3/2004 | Engerant | |
| 6,705,541 B2 | 3/2004 | Schuehrer et al. | |
| 6,714,725 B2 | 3/2004 | Grone et al. | |
| 6,722,578 B2 | 4/2004 | Skalitzky et al. | |
| 6,730,311 B2 | 5/2004 | Maleeny et al. | |
| 6,749,672 B2 | 6/2004 | Lynn | |
| 6,790,436 B2 | 9/2004 | Williams et al. | |
| 6,808,791 B2 | 10/2004 | Curro et al. | |
| D498,524 S | 11/2004 | Morillas | |
| D498,525 S | 11/2004 | Harbutt et al. | |
| D498,836 S | 11/2004 | Morillas | |
| 2001/0030243 A1 | 10/2001 | Hurry et al. | |

| | | |
|---|---|---|
| 2003/0007887 A1 | 1/2003 | Roumpos et al. |
| 2003/0017129 A1 | 1/2003 | Maleeny et al. |
| 2003/0085297 A1* | 5/2003 | Huang .................. 239/34 |
| 2003/0089791 A1 | 5/2003 | Chen et al. |
| 2003/0094503 A1 | 5/2003 | Rymer et al. |
| 2003/0108703 A1 | 6/2003 | Lang |
| 2003/0152374 A1 | 8/2003 | Grone et al. |
| 2003/0168521 A1 | 9/2003 | Skalitzky et al. |
| 2003/0200690 A1 | 10/2003 | Galloway |
| 2003/0207787 A1 | 11/2003 | Dundale et al. |
| 2004/0000596 A1 | 1/2004 | Cuthbert |
| 2004/0057975 A1 | 3/2004 | Maleeny et al. |
| 2004/0094636 A1 | 5/2004 | Channer |
| 2004/0135000 A1 | 7/2004 | Buthier |
| 2004/0262418 A1 | 12/2004 | Smith et al. |
| 2004/0262421 A1 | 12/2004 | Hurry et al. |
| 2005/0145711 A1 | 7/2005 | Blondeau et al. |
| 2006/0225728 A1 | 10/2006 | Aktinson |

FOREIGN PATENT DOCUMENTS

| | | |
|---|---|---|
| EP | 0 645 081 | 7/2001 |
| EP | 1 346 734 | 9/2003 |
| GB | 3003643 | 11/2002 |
| GB | 3003644 | 6/2003 |
| GB | 3005817 | 7/2003 |
| GB | 3007046 | 9/2003 |
| GB | 3007049 | 9/2003 |
| GB | 3007052 | 9/2003 |
| GB | 3007053 | 9/2003 |
| GB | 3007054 | 9/2003 |
| GB | 3007055 | 9/2003 |
| GB | 3007056 | 9/2003 |
| GB | 3007057 | 9/2003 |
| GB | 3007233 | 9/2003 |
| GB | 3007045 | 10/2003 |
| GB | 3007048 | 10/2003 |
| GB | 3012024 | 2/2004 |
| GB | 3012025 | 2/2004 |
| GB | 3012026 | 2/2004 |
| JP | HA05015803 | 8/1993 |
| JP | D1027932 | 9/1998 |
| JP | D1195937 | 2/2004 |
| NL | 000194709-0001 | 9/2004 |
| NL | 000205661-0001 | 10/2004 |
| NL | 000252358-0001 | 2/2005 |
| NL | 000252366-0001 | 2/2005 |
| WO | WO 00/23121 | 4/2000 |
| WO | WO 03/068276 | 8/2003 |

OTHER PUBLICATIONS http://www.glade.com/plugins.asp.
http://www.airwick.us/product page/product.html.
http://www.racerwheel.com/tcr-cz-103.html.
http://www.racerwheel.com/tcr-cz-102a.html.
http://www.giftsandgadgetsonline.com/ioairfrwilif.html.
http://www.allproducts.com/gift/sundeal/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor eliminating light bulbs.html.
Int'l. Search Report and Written Opinion dated Jul. 4, 2006: Appl. No. PCT/US2005/023227.

* cited by examiner

VOLATILE MATERIAL EXPIRATION INDICATING SYSTEM

FIELD OF THE INVENTION

The invention generally relates to indicators for expiration of usable materials. More specifically, the invention relates to an expiration indicator of a dispenser for volatile materials that permits a more desirable appearance than the prior art.

BACKGROUND

This application is related to the following co-pending applications filed concurrently herewith: Volatile Material Dispensing System, Ser. No. 10/881,816 and Volatile Material Dispensing System with Illuminating Means, Ser. No. 10/880,885.

BACKGROUND ART

A variety of packages have been used to contain volatile materials and permit the controlled dispensing of them as vapors into the ambient air. The prior art describes in detail the use of permeable membranes as well as other manners to disperse volatile material from a given container. A number of the volatile material dispensers have also utilized various forms of expiration or use-up indicators.

U.S. Pat. No. 5,259,555 describes a wooden air freshener with fragrance loading chamber. Air freshening oil is placed in a chamber and migrates through the wood along the capillaries of the wood grain until it reaches the outside wooden surface of the container. The wood acts as a metering device for the gradual release of the air freshening agent. As the oil evaporates, the wooden member loses its luster and lightens in appearance, signaling that more air freshening agent is needed. This change in appearance allows an observer to easily determine whether the chamber needs to be refilled.

U.S. Pat. No. 6,555,068 describes an apparatus incorporating air modifying agents. This air modifying agent and an electrolyte are entrained in a gel-based aqueous reservoir which contacts a pair of electrodes. The extent of exhaustion of the air modifying agent from the reservoir corresponds to the extent of exhaustion of electrode activity, whereby the operability of the electrical device indicates the presence of air modifying agent in the reservoir.

U.S. Pat. No. 4,293,095 describes an air treating device having an indicator system to signal exhaustion of the operative fluid.

U.S. Pat No. 2003/0089791 describes a vaporization indicator film. During use, the semi-porous membrane visually indicates transmission of active ingredient vapor to the consumer through use of pores that are normally opaque and become saturated and turn from opaque to clear when in use. Upon depletion of the volatile material from the reservoir and subsequently from the membrane, the membrane turns opaque again.

It is known in the art to utilize fumed silica gelling agents to provide an expiration indicator for solution-diffusion delivery systems. With respect to these systems, the silica particles are suspended in the active volatile liquid, and as the active liquid diffuses, the concentration of the silica particles increases. Following a period of time and near the expiration of such a device, a cracked residue results and the contents of the dispenser are cracked and crumbly to indicate a level of expiration. This appearance is unattractive and unpleasant.

Prior art volatile material dispensers utilize tray-like holders that are formed from thermoformed plastic materials. Volatile material in these holders contains a fumed silica gelling agent that is blended with the fragrance and suspended in the volatile material. Subsequent to exhaustion of the volatile material the fumed silica agent remains leaving a unattractive appearance. Fumed silica increases the viscosity of the volatile material. As volatile material exhaustion occurs the concentration of the agent increases as well as viscosity, which solidifies the remaining material and prevents it from easily migrating within the holder. As a result of using these silica gelling agents, a relatively deep tray-like holder is necessary. A vapor void forms in the deep tray-like holder and the silica gel fills up in the vapor filled chamber, crumbles and adversely affects active ingredient diffusion. As the volatile material is diffused through the membrane the silica gelling agent remains. The presence of the silica gelling agent interferes with the surface area contact of the remaining volatile material and the membrane. This reduction of surface area contact affects the diffusion rate of the volatile material. The reduced diffusion rate prevents the volatile material from diffusing at a constant or nearly constant rate up until approximate expiration. As a result, the diffusion of volatile material is substantially less than 100%. In prior art dispensers, approximately 50–60% diffusion was customary. An improved volatile material holder is needed that will provide an accurate indication of volatile material expiration and provide an efficient, steady and predictable level of diffusion. Part of the problem with the prior art is that the level of diffusion decreases substantially as the expiration of the dispenser approaches. The present invention solves this problem by providing for an evacuatable and shallower volatile material dispenser that increases the surface area contact between the membrane and the volatile material. Prior art air freshener dispensers can be clearly identified as such, leading to a social stigma. The present invention presents a decorative displaying means which prevents this socially detrimental stigma. The present invention solves this problem and solves the problem of knowing when the dispenser is close to expiration or already expired.

SUMMARY OF THE INVENTION

In accordance with a first aspect of the invention, a volatile material expiration indicating system is provided that includes an evacuatable volatile material dispenser, including a blister having a first surface and a vapor permeable membrane sealed to a periphery of said first surface. The volatile material is comprised of an active ingredient, thickening agent and a colored dye, wherein diffusion of the volatile material through the permeable membrane results in a pressure gradient between the ambient atmosphere and the dispenser. As the volatile material leaves the blister, the blister transitions from a first filled condition to a second collapsed condition. The vacuum forces within the blister hold the membrane against the surface of the volatile materials as they decrease in quantity in the blister, and thereby provide a sustained surface area contact between the membrane and the volatile material.

In accordance with another aspect of the invention, the indicating system further comprises a vapor impermeable laminate releasably connected to the vapor permeable surface, wherein the laminate prevents the diffusion of said volatile substance. The laminate may be peeled from the dispenser in order to start the diffusion of the volatile material through the membrane.

In accordance with a third aspect of the invention, the indicating system further includes a displaying means wherein the displaying means is a translucent frame structure having a transparent wall, a front side and a back side. The blister is attached to the back side of the frame and can be viewed through the transparent wall. The volatile material contained within the blister may be colored with a dye, and said color would be used in conjunction with the indicating system to act in a decorative manner.

In accordance with another aspect of the invention, the displaying means further includes a decorative image, wherein said image is viewable throughout said system's life cycle.

Other features will become apparent to those skilled in the art from a review of the following detailed description, taken in conjunction with the drawings and the appended claims. While the disclosed dispenser is susceptible of embodiments in various forms, described below are specific embodiments that are intended as illustrative (and not intended to limit the disclosure to the specific embodiments described herein).

DETAILED DESCRIPTION

Figure 1:
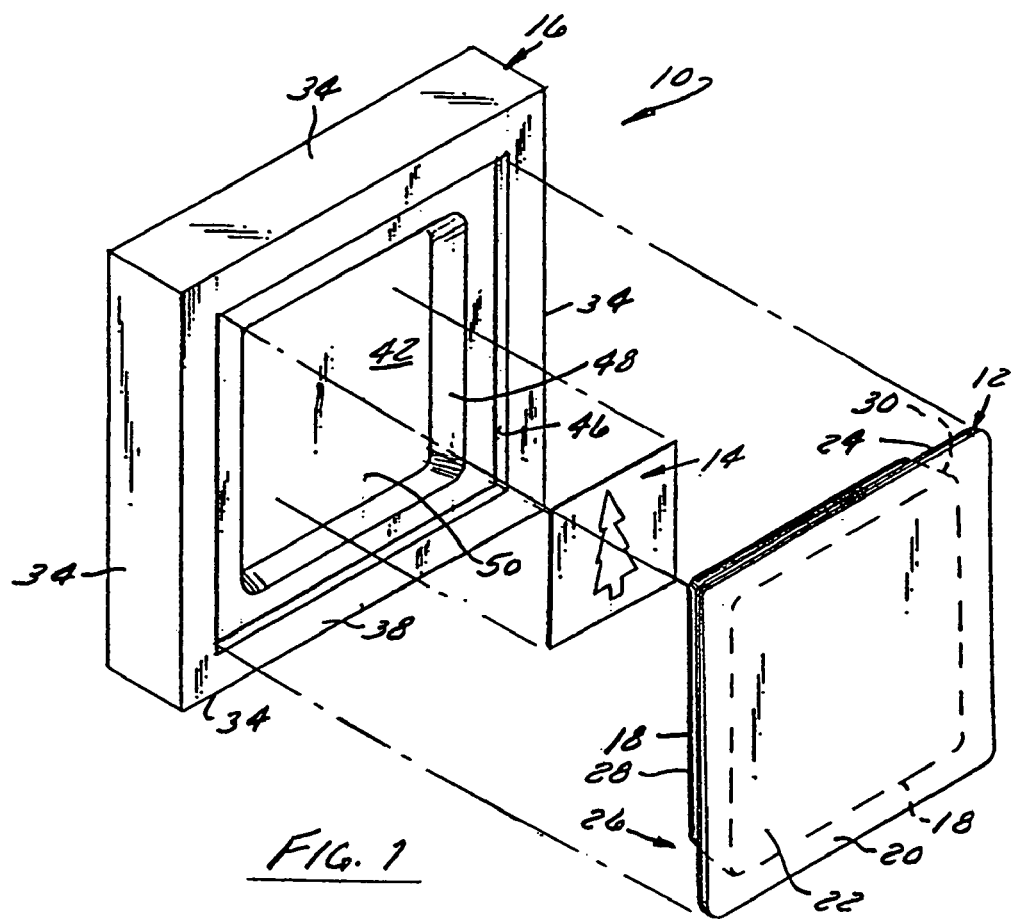
FIG. 1 is an exploded back perspective view of the system.
Figure 2:
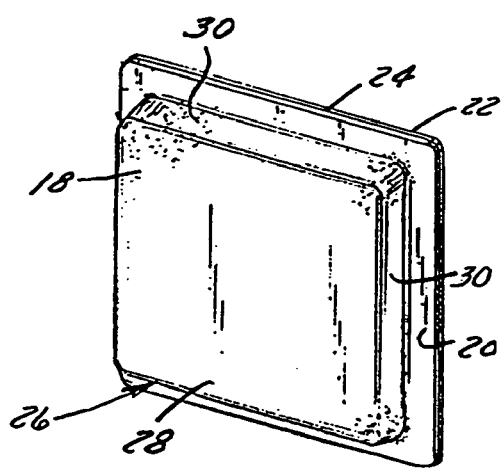
FIG. 2 is a perspective view of the dispenser shown in FIG. 1.

Referring to FIGS. 1 and 2, a volatile material expiration indicating system 10 is illustrated, the system 10 having an evacuatable material dispenser 12, a decorative image 14, and a display frame 16 for holding the dispenser 12. The decorative image 14 is attached to the frame 16.

Figure 7:
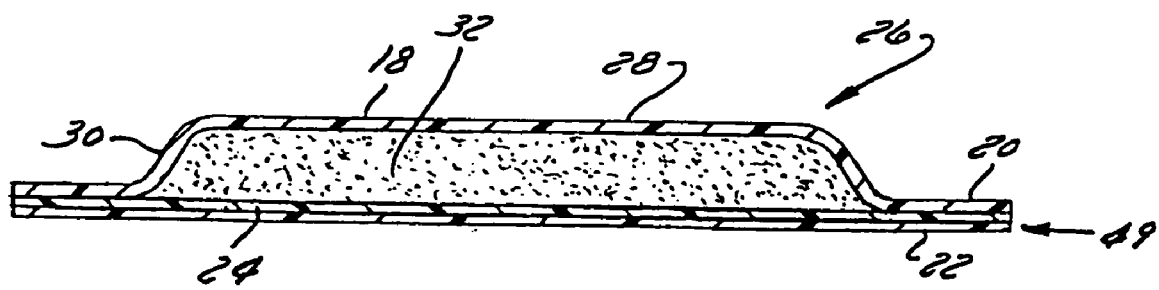
FIG. 7 is a partial enlarged sectional view of the dispenser shown in FIG. 6.

The dispenser 12 includes a blister 18, a peripheral flange 20, and an impermeable laminate 22 releasably adhered to said blister 18. The blister 18 includes a non-porous permeable membrane 24 comprised of low density polyethylene (LDPE), and a cup-shaped structure 26. Cup 26 includes a recycled polyethylene terephthalate (RPET) layer adhesively bonded to a nylon laminate. The nylon laminate includes a layer of ethylene vinyl acetate (EVA) coextruded to each side of a middle nylon layer. The cup 26 includes a bottom wall 28 and four side walls 30, that in conjunction with the membrane 24 acts as a sealed reservoir to contain the volatile material 32 (FIG. 7).

The laminate 22 includes a layer of polypropylene, aluminum foil, and polyester. The polypropylene is adhesively bonded to the aluminum foil layer, which is adhesively bonded to the polyester layer. An extrusion bonding material is used to bond the layers together. Laminate 22 preferably has a thickness of between 0.1 to 0.2 mm. The polyester layer is suitable for printing and is the outer surface of laminate 22. Preferably the membrane 24 and polypropylene layer of laminate 22 are coextruded when the blister is manufactured. The coextrusion permits for the laminate 22 to be peelably removed from the blister 18 while avoiding unnecessary reactions between an adhesive and the volatile material 32 during diffusion.

Cup 26 preferably has a thickness between 0.3 to 0.4 mm. The cup 26 is generally rectangular and preferably square with overall dimensions of about 3–5 mm thick, 50–60 mm long and 50–60 mm wide. Each of its four sidewalls 30 has a corresponding width of 3–5 mm and a length of 50–60 mm. Sidewalls 30 taper slightly outward as one moves from the bottom wall to the flange 20. Bottom wall 28 is also generally rectangular and has width of 48–58 mm and a height of 48–58 mm. The sidewalls 30 and bottom wall 28 of cup 26 are preferably thermoformed from a single sheet of the RPET and nylon laminate that is heated, then either blown or pressed into the flange-and-cup arrangement shown in the FIGURES. Preferably the cup 26 is clear and translucent, allowing for the visibility of the volatile material 32 contained within the blister 18.

Cup 26 contains relatively shallow side walls 30, as stated above. The shallow nature of the blister 18 allows for the membrane 24 to collapse upon the bottom wall 28. Diffusion of the volatile material 32 through the membrane 24 creates collapsing of membrane 24 upon wall 28 that maintains contact between the volatile material 32 and the membrane 24. The contact allows for a greater percentage of overall volatile material 32 diffusion and allows for indication of volatile material 32 expiration.

Peripheral flange 20 is preferably planar. It is coupled to and extends outward from the top edges of the cup 26 (e.g. the upper edges of sidewalls 30). Flange 20 is integrally formed with the cup 26 in a thermoforming process, as described in the preceding paragraph.

Following placement of the volatile material 32 into the cup 26, a seal is made between the flange 20 and the permeable membrane 24 thereby forming the dispenser 12. At the same time laminate 22 may be attached to the blister 18 by having already been adhered to the membrane 24. The membrane 24 and laminate 22 may be attached to the flange 20 of the blister 18 using any conventional means, such as an adhesive, heat sealing, crimping, or the like. The seal must be air-tight so as to prevent leakage of air or volatile material 32. Most preferably the membrane 24 and the laminate 22 are sealed to the cup 26 in a single step. The volatile material 32 does not completely fill the void within the blister 18. A relatively small amount of air can be tolerated in dispenser 12 following the creation of blister 18. Preferably the air in the sealed blister is no more than 3–6% of the overall volume of the blister 18. As the volatile material diffuses out of dispenser 12 no air enters the blister 18 through the permeable membrane 24. The membrane 24 is configured to distend and collapse without passage of air into the dispenser.

When the volatile material is to be dispensed, the laminate 22 is removed from the blister 18. Preferably, the removal process will occur by a user grasping an end of the laminate 22 and peeling it off the blister 18. A tab, extension, or other means for grasping (not shown) may be included as an extension of the laminate 22 to aid in removal of the laminate 22. The extension may be at the corners, ends, or on the surface of the laminate 22.

Permeable membrane 24 has a thickness of about 0.05 to 0.15 mm and has a density preferably between 0.88 and 0.95 grams/cubic centimeter. It is formed integrally with laminate 22 and is heat fused to flange 20 such that membrane 24 extends across the entire cup 26. Membrane 24 encloses and seals the cup 26 with the volatile material 32 stored inside thereby forming a thin sealed container impermeable to the volatile material 32 stored inside. This container remains impermeable until the user grasps a corner of laminate 22 and peels laminate 22 from the membrane 24, thereby exposing permeable membrane 24 and permitting the volatile material 32 to migrate through the permeable membrane 24 and diffuse into the ambient air. The membrane 24 is preferably comprised of LDPE and is clear and translucent, allowing for visibility of the volatile material contained within the blister 18.

Frame 16 is a rectangular structure, preferably square, with four substantially equal-sized side walls 34, a front face 36 (FIG. 4) and a rear face 38. Frame 16 preferably has a thickness of between 12 and 22 mm and a height and width of between 70 and 90 mm. More preferably frame 16 has a width of approximately 15 mm and height of approximately 80 mm.

Figure 4:
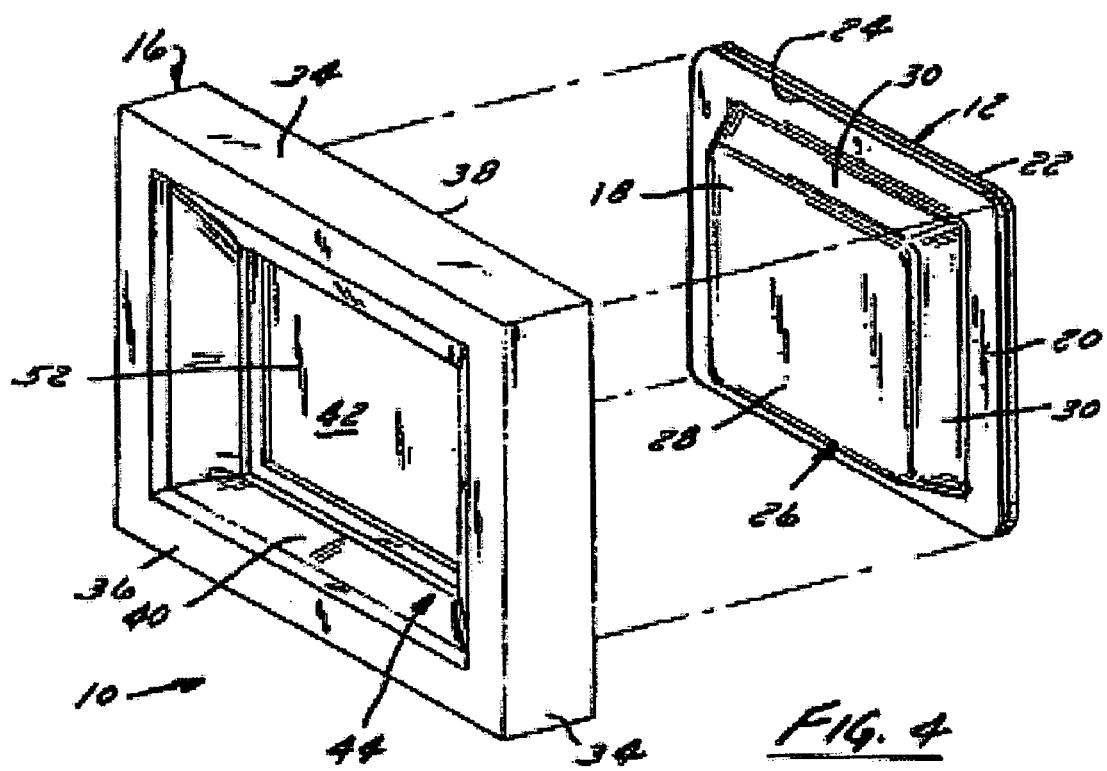
FIG. 4 is an exploded front perspective view of the system.
Figure 5:
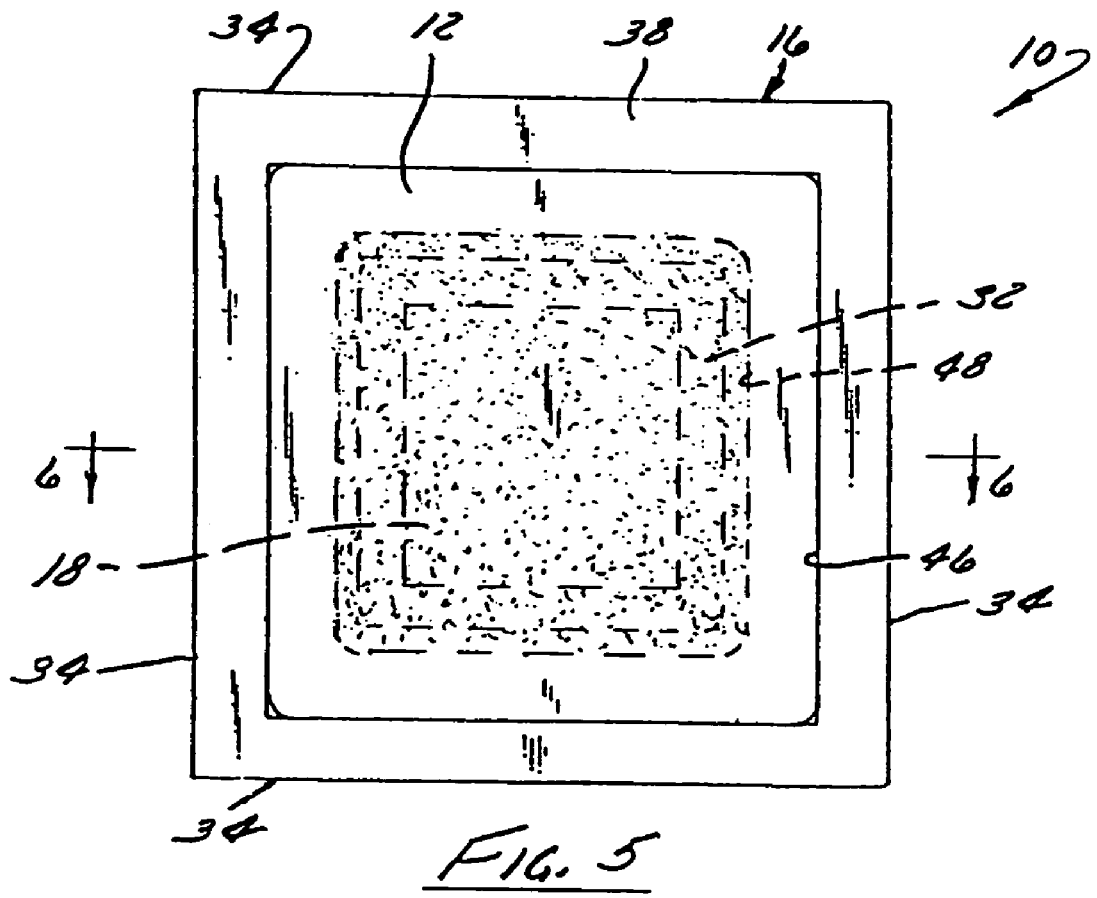
FIG. 5 is a back face view of the system with a dispenser in the first filled condition.
Figure 6:
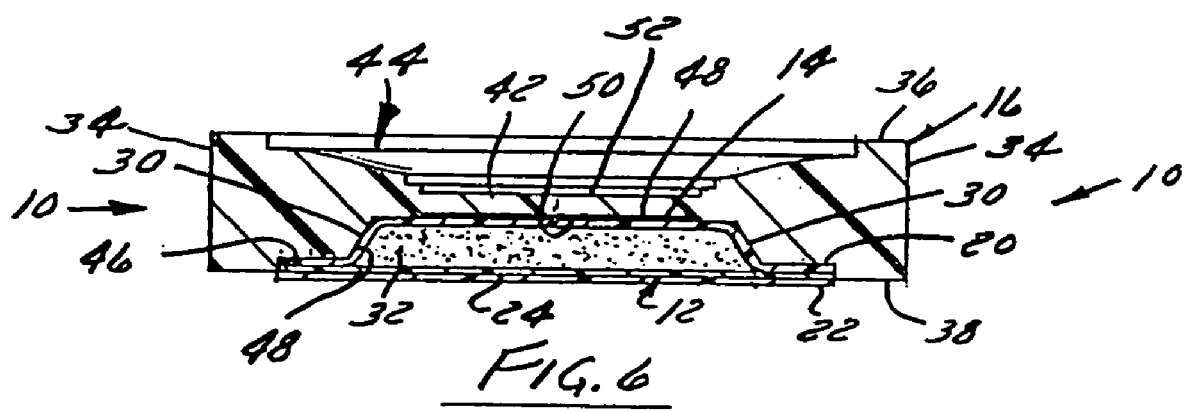
FIG. 6 is a sectional view of the system taken substantially along line 6—6 of FIG. 5.
Figure 9:
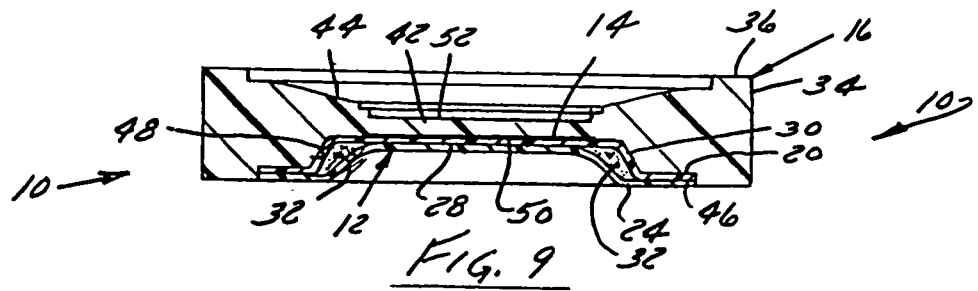
FIG. 9 is a sectional view of the system taken substantially along line 9—9 of FIG. 8.
Figure 10:
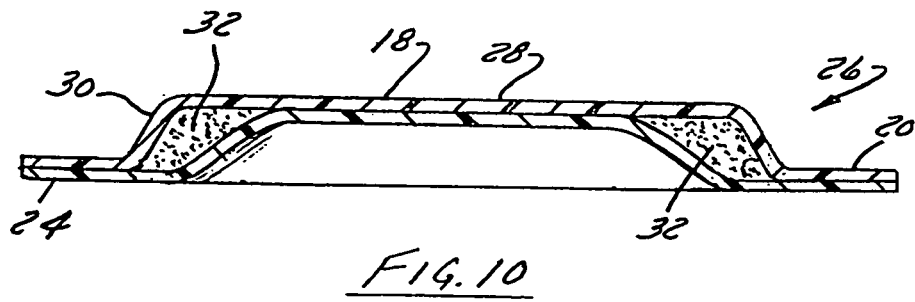
FIG. 10 is a partially enlarged sectional view of the system shown in FIG. 9.
Figure 11:
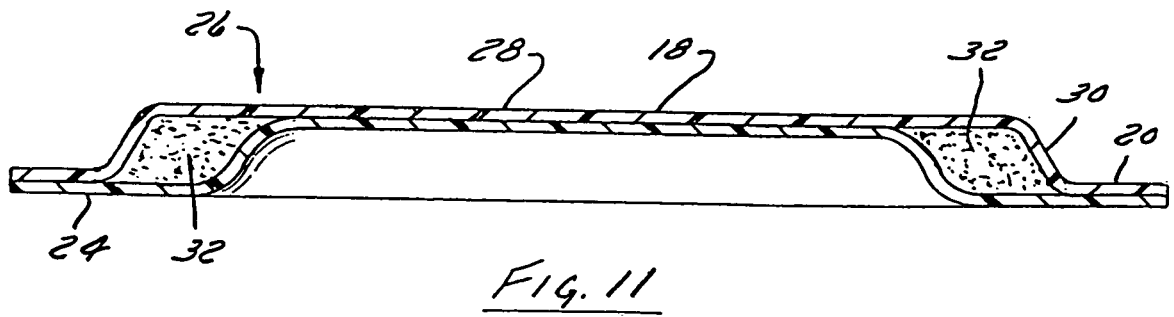
FIG. 11 is a partially enlarged sectional view of the dispenser taken substantially along line 11—11 of FIG. 8.

Front face 36 has a stepped recess 40 (FIG. 4). Recess 40 gives frame 16 the appearance of a picture frame surrounding and framing the bottom (or back) wall 42 (FIG. 4) of the recess 40. In the preferred embodiment, shown in FIGS. 6 and 9, the walls of recess 40 appear in cross section to have steps or curves 44 in the manner of an ornate picture frame. The recess 40 preferably centered in the front face 36 and is disposed away from the side walls 34. The recess 40 does not extend to the edge of the front face 36. Instead, front face 36 appears as a border extending around the edges of the recess 40, having a constant width between 2 and 4 mm.

Wall 42 is preferably transparent or translucent to permit light to pass through. Wall 42, in that regard, may function as a window that permits the viewer (from the front) to visually perceive what is directly behind wall 42.

Rear face 38 of frame 16 also is recessed. This recess is similarly stepped, and is configured to completely receive dispenser 12, with dispenser 12 positioned so that the membrane 24 surface is substantially flush with rear face 38. The recess is also preferably stepped, having a shallower peripheral recess 46 extending all the way around rear face 38 and a deeper central recess 48. The deeper central recess 48 is configured and dimensioned to receive cup 26, and the peripheral recess 46 is configured and dimensioned to receive and support flange 20. In short, the central recess 48 and peripheral recess 46 combined have a negative shape that is the same as that of dispenser 12.

Peripheral recess 46 preferably has an adhesive, spring clip, or other mechanical or adhesive retaining means that is configured to hold flange 20 in place. Flange 20 and peripheral recess 46 may be adhered to one another through the use of any adhesive, or alternatively though a mechanical means, such as interference fit, or separate mechanical fastener, such as a spring clip. When an adhesive 49 is used (as shown herein), a flange-to-frame adhesive may be chosen to either permanently adhere the flange 12 to the display frame 16 or, alternatively, be releasably adhered for easy removal. In this manner, frame 16 can be a permanent and reusable item to which a succession of replacement dispensers 12 are affixed and later removed and replaced.

Central recess 48 is deeper than peripheral recess 46 since it must accommodate the greater combined thickness of cup 26, flange 20 and membrane 24. The bottom of cup 26 is adjacent to and preferably slightly spaced apart from the bottom 50 of central recess 46. Central recess 48 and peripheral recess 46 are preferably centrally spaced from the internal edges of rear face 38.

Figure 3:
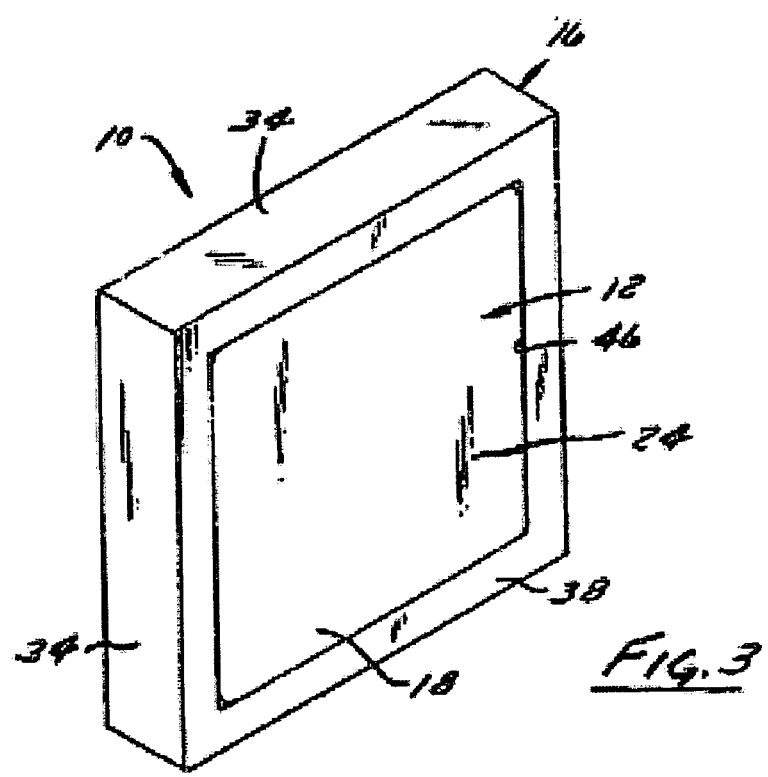
FIG. 3 is a perspective view of the assembled system shown in FIG. 1.

The distance between the bottom 50 (FIG. 1) of central recess 48 and the bottom 52 (FIG. 4) of recess 40 on the front face 36 of frame 16 (i.e. the thickness of wall 44), is preferably between 2 and 5 mm. Wall 42 may be transparent or translucent. The translucent properties of wall 42 enables the user to easily identify when the volatile material 32 has nearly all diffused through membrane 24. Additionally, the translucent properties of wall 42 have a decorative function. The frame is best shown (FIGS. 3 and 4) to represent the translucent properties of wall 42.

The display frame 16 may be constructed from a variety of compositions, including glass, injection-molded plastic, and rubber. In the preferred embodiment, the display frame 16 is constructed from molded glass that is clear and transparent.

Blister 18 of the dispenser 12 is filled with a volatile material 32. It is particularly suited for use in holding a volatile material 32 comprising an active ingredient, which is to be slowly diffused into the surrounding atmosphere, such as a fragrance, air freshener, insect repellant insecticide. In addition to the active ingredient the preferred embodiment includes a dye and thickening agent that color and thicken the volatile material 32. The dye and thickening agent most preferably comprise less than 2% of the overall composition.

Insecticides and other related chemicals may also be utilized as the volatile material 32. Where the user does not wish to have an unsightly insect repellant device, but requires the utility of a repellant, the decorative system is advantageous and blends in with the surrounding décor. The indicator system 10 allows for such a volatile material 32 to be released while having a decorative appearance.

When volatile material 32 is a fragrance, the fragrance can be relatively simple in composition, or can be a complex mixture of natural and/or synthetic chemical compounds. Various mixtures of volatile materials for use in the indicator system may comprise as few as two chemicals and as many as over one hundred. Most conventional fragrance materials are synthetic or naturally derived volatile essential oils, such as, for example, lemon, mandarin, cedar leaf, clove leaf, cedar wood, oil of bergamot, bitter orange, geranium, lavender, orange, lavandin, neroli, rose absolute, cinnamon, and the like. Synthetic types of fragrance composition, either alone or in combination with natural oils, are described in U.S. Pat. Nos. 4,314,915; 4,411,829; and 4,434,306, which are incorporated herein by reference.

Figure 8:
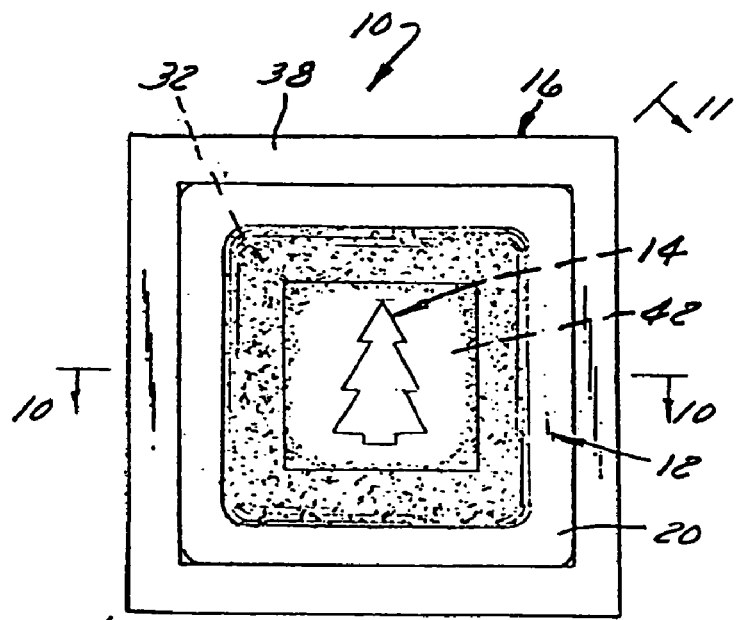
FIG. 8 is a front face view of the system with a partially evacuated dispenser.

The image 14 (FIGS. 1 and 8) may be graphic or textual. It may read, for example, "Please Replace." The image may be positioned in a plurality of positions, including but not limited to the following: front face 36 of frame, rear face 38 of frame, or upon the bottom wall 28 (FIG. 4). The image may be printed upon a layer of primed polyester that is adhesively adhered to the system 10, as described above. Alternatively, the image may be thermoformed into the bottom wall 28 or may be molded into the decorative frame 16.

The image 14 is shown in the shape of a tree, but may also be chosen from festive images used during various holiday seasons, such as a Christmas tree, menorah, Easter egg, valentine heart, pumpkin, and the like. Additionally, the color of the volatile material may be chosen in conjunction with such images to aid in celebration of the respective holidays. Multiple color combinations may be utilized in accordance to the decorative tastes of the user. The image 14 may be a plurality of other images that may include flowers, wildlife, cosmic displays, sporting related, and the like.

Depending upon the type and amount of dye utilized in conjunction with the volatile material 32 and the positioning of the image 14, either in front of or behind volatile material 32, the image 14 may or may not be viewable when the blister 18 is filled. Preferably the image is not viewable until a majority of the volatile material 32 has been released, and the dispenser 12 nears an empty or second condition, so as to more clearly indicate use-up of the volatile material 32. Most preferably, the image 14 is viewable when the dispenser 12 is full, empty, and at any point in between. However, the image 14 would be more readily viewable when the dispenser 12 is empty, in order to enhance the decorative nature in conjunction with dispenser 12 use-up. For purposes of the present invention, expiration of the volatile material 32 or system 10 refers to use-up of the volatile material 32.

The preferred embodiment of the invention allows for the indication that the dispenser 12 is empty or near empty and little or no volatile material 32 remains. The indication of expiration is easily viewed following the near complete diffusion of the volatile material 32. However, diffusion of the volatile material 32 is dependent upon the type of membrane utilized. Preferably dispenser 12 will last 30–45 days before it is empty. Of course, this can be changed based upon the material used as a membrane, the thickness of the membrane, surface area of the membrane, volume of the blister 18, volume of volatile material 32 when the dispenser 12 is filled, and which particular volatile material composition is utilized.

When packaged the dispenser 12 is filled (FIG. 7) with volatile material 32 and laminate 22 is adhered to the permeable membrane 24. There is virtually no diffusion of volatile material 32 when the dispenser is filled and laminate 22 covers membrane 24. Following removal of laminate 22, the system 10 begins to transition towards an empty or second condition. Of course, there may be a small amount of volatile material 32 that remains and the dispenser 12 will be considered to have reached the second condition. As the volatile material 32 diffuses through the membrane 24, the membrane 24 slowly collapses upon the bottom wall 28. Following diffusion of the volatile material 32 across the membrane 24 there is less material 32 contained within dispenser 12. Virtually no new air enters the dispenser 12 subsequent to diffusion of volatile material 32. The result of this is a pressure gradient across the membrane 24, with a higher pressure existing in the ambient air than the pressure in dispenser 12. The pressure gradient causes the ambient air to exert a net positive pressure upon the dispenser, which presses the membrane 24 against the remaining volatile material 32 and ultimately the bottom wall 28. Continued diffusion of the volatile material 32 increases the force exerted upon the membrane 24, which causes the remaining volatile material to migrate from a center of wall 28 towards the periphery of wall 28. Continued migration and diffusion of the volatile material 32 results in an increasing surface area contact between membrane 24 and wall 28 until dispenser 12 is empty, or nearly empty. Increasing contact between the membrane 24 and the wall 28 allows for the image 14 to be more readily viewable. The pressure gradient ultimately resulting in migration of the volatile material 32 may also be viewed as occurring due to an increasing compressed vacuum presence within dispenser 12 as the volatile material continues to diffuse across membrane 24.

Referring to FIGS. 8–11, a small amount of volatile material 32 remains within the dispenser 12 when it is nearly empty, and is present in the form of a ring-like appearance towards the periphery of the bottom wall 28. A dye and thickener combine to comprise approximately 2% of the overall volatile material composition of the system 10 at the first condition. Preferably a higher concentration of dye is present in the volatile material 32 when the dispenser 12 is nearly empty, as the dye substantially does not diffuse across membrane 24. This results in a more readily viewable ring-like appearance. The color of the ring-like image is more intense in color than the coloration of the first condition because of the increased concentration of dye material. In the second condition the thickener and dye comprise nearly all of the material left within the dispenser 12. Of course, this may change dependant upon the particular dye composition and thickening agent utilized in the volatile material 32. As the system 10 approaches and is in a second condition, the nearly expired dispenser 12 can be seen so as to indicate its end of life.

When the dispenser 12 is full, or in the first condition, a decorative image may not be seen through the colored or opaque volatile material 32. As the dispenser 12 empties, or reaches the second condition, the decorative image 14 becomes viewable indicating a level of expiration or use-up. Alternatively, the decorative image 14 may be viewable while the dispenser 12 is both full and empty. Indication of volatile material 32 use-up may be achieved by more readily viewing image 14 as a result of the absence of colored volatile material within the dispenser 12. Dependent upon the specific volatile material composition, there may be numerous chemicals that either do not diffuse through the permeable membrane 24 or diffuse slower than the designed active ingredients or fragrances. Active ingredients may include chemicals such as esters, aldehydes, ketones, terpenes, alcohols, and aromatic compounds. As a result, material may be left within the blister 18 as it is nearly at or reaches a level of expiration in which replacement is necessary.

It is understood that the present invention is not limited to the embodiments described above and illustrated herein, but encompasses any and all variations falling within the scope of the appended claims.

INDUSTRIAL APPLICABILITY

The invention provides a volatile material exhaustion indicating system for volatile material dispensers.

We claim:

1. A volatile material expiration indicating system, comprising:
    an evacuatable volatile material dispenser, comprising a blister having a first surface and a vapor permeable membrane sealed to a periphery of said first surface;
    a volatile material contained within said blister, wherein said material is comprised of an active ingredient, thickening agent and a colored dye, wherein diffusion of at least one of the active ingredient, thickening agent, and colored dye through said permeable membrane results in a pressure gradient between the ambient atmosphere and said dispenser, wherein said blister transitions from a first filled condition to a second collapsed condition; and
    displaying means including a decorative image, wherein said decorative image is viewable at any point from and including said first condition to said second condition, and wherein the dispenser is affixed to the dispensing means.

2. The indicating system of claim 1 wherein the material dispenser further comprises a vapor impermeable laminate releasably connected to the vapor permeable membrane, wherein said laminate substantially prevents the diffusion of said volatile material.

3. The indicating system according to claim 1 wherein said displaying means is a translucent frame structure and further comprises a transparent window.

4. The indicating system of claim 1 wherein a flange is integrally connected to and extends from the periphery of said blister.

5. The indicating system of claim 1 wherein said blister is selected from the group of geometric shapes consisting of a rectangle, an oval, a circle, a square, and a trapezoid.

6. The indicating system of claim 1 wherein said permeable membrane is collapsible upon said first surface.

7. The indicating system of claim 1 wherein said dispenser is releasably affixed to said displaying means.

8. The indicating system of claim 1 wherein said image is viewable subsequent to a predetermined amount of volatile material diffusion.

9. The indicating system of claim 1, wherein said volatile material comprises a dispensing liquid.

10. The indicating system of claim 9, wherein said dispensing liquid is a diffusible fragrance.

11. The indicating system of claim 9, wherein said dispensing liquid is a diffusible insecticide.

12. A volatile material expiration indicating system, comprising:
   an evacuatable volatile material dispenser, comprising a blister having a first surface and a vapor permeable membrane sealed to said first surface;
   a dispensing liquid contained within said blister, wherein said liquid is comprised of a volatile liquid and a colored dye, wherein diffusion of said volatile liquid through said permeable membrane results in a pressure gradient between the ambient atmosphere and said dispenser, wherein said blister transitions from a first filled condition to a second collapsed condition; and
   a displaying means including a decorative image that is viewable subsequent to a predetermined level of volatile liquid diffusion, wherein said dispenser is affixed to said displaying means.

13. The indicating system according to claim 12 wherein said displaying means is a translucent frame structure and further comprises a transparent window.

14. The indicating system of claim 12 wherein the material dispenser further comprises a vapor impermeable laminate releasably connected to the vapor permeable membrane.

15. The indicating system of claim 12 wherein a flange is connected to and extends from the periphery of said blister.

16. The indicating system of claim 12 wherein said permeable membrane is collapsible upon said first surface.

17. The indicating system of claim 12 wherein said dispenser is releasably affixed to said displaying means.

18. The indicating system of claim 12 wherein said decorative image is viewable upon a requisite level of volatile liquid diffusion.

19. The indicating system of claim 12 wherein said dispensing liquid is a diffusible fragrance.

20. The indicating system of claim 12 wherein said dispensing liquid is a diffusible insecticide.

21. A volatile material expiration indicating system, comprising:
   an evacuatable volatile material dispenser, comprising a liquid retaining reservoir having a first surface, a vapor permeable surface opposite said first surface, side walls connecting said first surface to said vapor permeable surface, and a flange extending laterally from a periphery of said reservoir;
   a volatile material contained within said reservoir, wherein said material is comprised of a volatile liquid, wherein diffusion of said volatile material through said permeable surface results in a pressure gradient between the ambient atmosphere and said reservoir; and
   a displaying means including a transparent wall and a decorative image disposed thereon, wherein said dispenser is affixed to said displaying means.

22. The indicating system of claim 21 wherein said volatile material contains a dye.

23. The indicating system according to claim 21 wherein said displaying means is transparent.

24. The indicating system of claim 21 wherein said permeable surface is collapsible upon said first surface.

25. The indicating system of claim 21 wherein said dispenser is releasably affixed to said displaying means.

26. The indicating system of claim 21 wherein said decorative image is viewable upon a requisite level of volatile liquid diffusion.

27. The indicating system of claim 21 wherein said reservoir is substantially evacuated of air.

28. A method for indicating the expiration of a volatile liquid dispenser comprising the steps of:
   removing a non-permeable cover laminate from a dispenser;
   placing said dispenser in an optimal viewing position;
   allowing a volatile liquid to diffuse from a reservoir and through a membrane;
   viewing said dispenser at periodic time intervals; and
   removing said dispenser after the volatile liquid has diffused through the membrane, leaving a reduced amount of the volatile liquid at the periphery of said reservoir, wherein said volatile liquid is colored and is forced to the reservoir periphery through an internal vacuum force.

* * * * *

UNITED STATES PATENT AND TRADEMARK OFFICE
CERTIFICATE OF CORRECTION

PATENT NO. : 7,188,780 B2
APPLICATION NO. : 10/880634
DATED : March 13, 2007
INVENTOR(S) : Edward J. Martens, III It is certified that error appears in the above-identified patent and that said Letters Patent is hereby corrected as shown below:

Column 8: Line 66, replace "dispensing" with --displaying--

Column 10: Line 29, replace "transparent" with --translucent--

Signed and Sealed this

Eighth Day of September, 2009

David J. Kappos
*Director of the United States Patent and Trademark Office*